US00PP17740P3

(12) United States Plant Patent
Roethling

(10) Patent No.: US PP17,740 P3
(45) Date of Patent: May 15, 2007

(54) EASTERN REDBUD PLANT NAMED 'HEARTS OF GOLD'

(50) Latin Name: *Cercis canadensis*
Varietal Denomination: Hearts of Gold

(76) Inventor: Jon L. Roethling, 4325 Pickwick Dr., Raleigh, NC (US) 27613

( * ) Notice: Subject to any disclaimer, the term of this patent is extended or adjusted under 35 U.S.C. 154(b) by 207 days.

(21) Appl. No.: 10/967,697

(22) Filed: Oct. 15, 2004

(65) Prior Publication Data

US 2006/0085878 P1 Apr. 20, 2006

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
*Assistant Examiner*—June Hwu

(57) ABSTRACT

'Hearts of Gold' is a distinctive variety of *Cercis canadensis,* which is characterized by its distinct bright golden foliage compared to other cultivars of *Cercis canadensis.* In addition, one-year-old whips of 'Hearts of Gold' produce flower buds, whereas other cultivars of *Cercis canadensis* generally only produce flowers on older plants. Further, first-year budded 'Hearts of Gold' trees appear to be more vigorous and uniform in growth than similar-aged trees of other known cultivars known to the inventor.

3 Drawing Sheets

Genus: *Cercis.* Species: *canadensis.*
Denomination: 'Hearts of Gold'.

BACKGROUND OF THE INVENTION

The present invention relates to a new and distinct cultivar of *Cercis canadensis,* commonly known as Eastern Redbud. The genus *Cercis* encompasses approximately eight species of deciduous, woody trees native to temperate portions of the eastern and western United States, eastern and central Asia, and the Mediterranean basin. *Cercis* is a member of the legume family (Fabaceae, or Leguminosae), within which it belongs to subfamily Caesalpinioideae, section Cercideae. Within this family, there are no other genera that are closely related to *Cercis,* and *Cercis* is believed to represent a Tertiary relic derived from a now-extinct ancestral genus.

The new cultivar is known botanically as *Cercis canadensis* and will be referred to hereinafter by the cultivar name 'Hearts of Gold'.

*Cercis canadensis* can be found from Maine and southern Canada, west to Michigan, Illinois, Iowa, and Nebraska, where it is referred to as *Cercis canadensis* var. *canadensis* and has the common name eastern redbud. On the southern end of its range, *Cercis canadensis* is native from Florida to Texas and south into northeastern Mexico. Plants found in north-central Texas and Oklahoma are referred to as *Cercis canadensis* var. *texensis* (formerly known as *Cercis reniformis*), commonly called Texas redbud. Plants occurring in southern Texas, northeastern Mexico, and New Mexico are known as *Cercis canadensis* var. *mexicana,* commonly called Mexican redbud. In the western range of Arizona, Utah, Nevada, and California, these plants are called *Cercis canadensis* var. *orbiculata* (recognized at the specific level as *Cercis orbiculata*) or commonly referred to as Arizona redbud. Until recently, plants growing in California have been recognized as *Cercis occidentalis* (western redbud), but this view is now being abandoned among legume taxonomists.

Parentage: 'Hearts of Gold' was discovered by the inventor in the spring of 2002 as an isolated seedling of *Cercis canadensis* (unnamed) growing under a cultivated (garden) setting at a private residence in Greensboro, N.C.

Comparisons with other *Cercis canadensis:* 'Hearts of Gold' is distinguishable from other cultivars of *Cercis canadensis* known to the inventor and from all other known *Cercis* taxa by the foliage color. Mature leaves of typical specimens of *Cercis canadensis* are dark blue-green and dull on the upper surface, lighter beneath. On new growth, most plants of *Cercis canadensis* bear light green, red-tinted leaves, whereas the new foliage growth of 'Hearts of Gold' is orange-red in color. On both the upper and lower leaf surfaces, new foliage color in a typical *Cercis canadensis* specimen will be light green. In contrast, 'Hearts of Gold' bears bright, yellow-green leaves. Further, flower buds of 'Hearts of Gold' are produced on one-year-old whips, whereas other cultivars of *Cercis canadensis* do not exhibit this trait and typically produce buds only after two to three years. Moreover, first-year budded 'Hearts of Gold' trees appear to be more vigorous and uniform in growth than similar-aged trees of other well-known cultivars of *Cercis canadensis,* such as 'Forest Pansy' (unpatented), 'Appalachia Red' (unpatented), 'Covey' (U.S. Plant Pat. No. 10,328) and 'Tennessee Pink' (unpatented).

Asexual reproduction. The new variety 'Hearts of Gold' was first asexually propagated under the inventor's direction by grafting budwood at Hidden Hollow Nursery, Belvidere, Tenn. in August 2002. The inventor grew off these first propagules and determined the characteristics of 'Hearts of Gold' were stable and were reproduced true to type. The inventor has since determined that 'Hearts of Gold' reproduces true to type in all successive generations of asexual reproduction.

SUMMARY OF THE INVENTION

The following traits have been repeatedly observed and represent the characteristics of 'Hearts of Gold'. These traits in combination distinguish 'Hearts of Gold' from all other varieties of *Cercis canadensis* known to the inventor. 'Hearts of Gold' has not been tested under all possible conditions and phenotypic differences may be observed with variations in environmental, climatic, and cultural conditions, however, without any variance in genotype.

1. *Cercis* 'Hearts of Gold' is a deciduous tree.
2. *Cercis* 'Hearts of Gold' exhibits upright stems and primary branches.
3. *Cercis* 'Hearts of Gold' exhibits smaller branches arching to produce a vase-to-rounded shaped canopy.
4. *Cercis* 'Hearts of Gold' has clusters of bright lavender sweet pea blooms in the early spring.
5. *Cercis* 'Hearts of Gold' leaves emerge orange-red then mature to bright gold.
6. *Cercis* 'Hearts of Gold' one-year-old whips produce flower buds.
7. *Cercis* 'Hearts of Gold' is hardy in U.S.D.A. Zone 5.

BRIEF DESCRIPTION OF THE DRAWINGS

The accompanying drawings illustrate the overall appearance of the new cultivar 'Hearts of Gold' showing the colors as true as it is reasonably possible to obtain in colored reproductions of this type. Colors in the photographs may differ from the color values cited in the detailed botanical description, which accurately describe the actual colors of the new variety of 'Hearts of Gold'.

DETAILED BOTANICAL DESCRIPTION OF THE VARIETY

Figure 1:
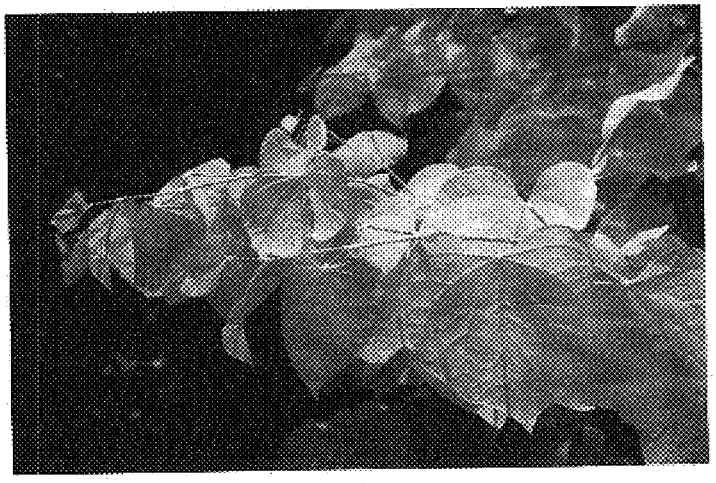
FIG. 1 illustrates the stem and foliage color of 'Hearts of Gold'.
Figure 2:
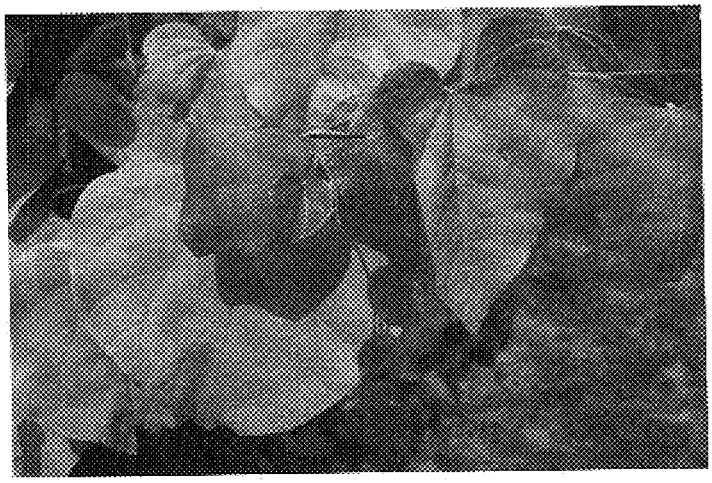
FIG. 2 illustrates the stem and foliage color of 'Hearts of Gold' and, in particular, shows the orange-red coloration of the new flush of growth.
Figure 3:
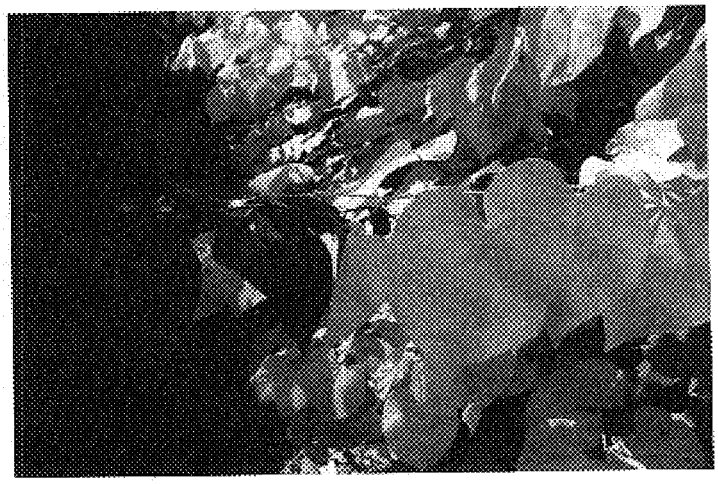
FIG. 3 illustrates the foliage color of 'Hearts of Gold' (right) compared to a *Cercis canadensis* 'Forest Pansy' (left; unpatented).
Figure 4:
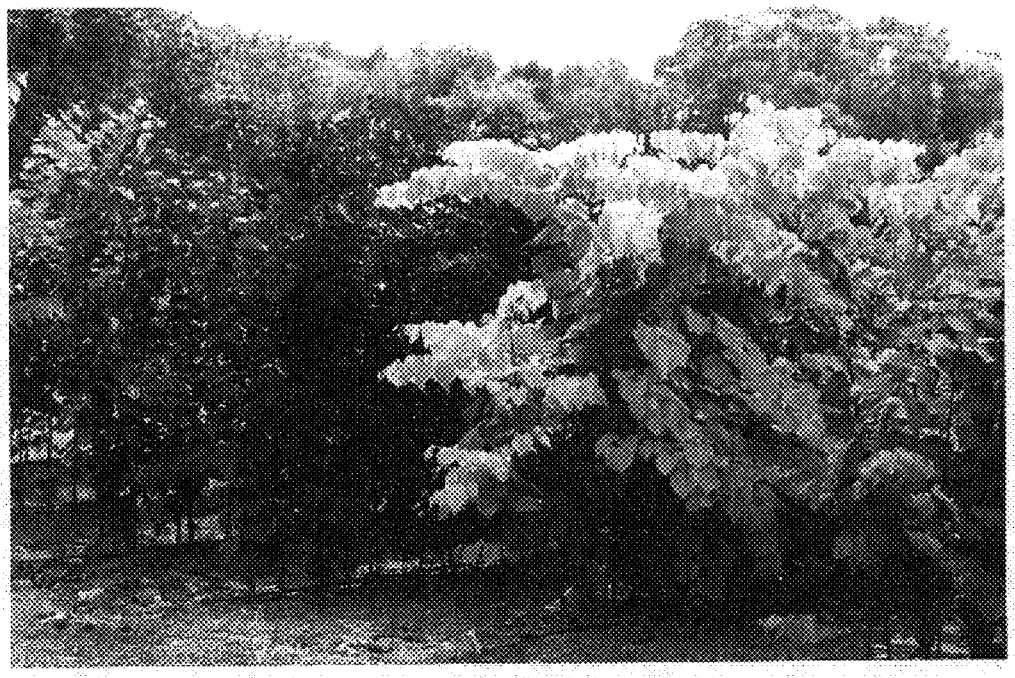
FIG. 4 illustrates the foliage color and form of 'Hearts of Gold' trees (center) as compared with *Cercis canadensis* 'Forest Pansy' (purple foliaged trees, left) and *Cercis canadensis* 'Appalachia Red' (green foliaged trees, right).
Figure 5:
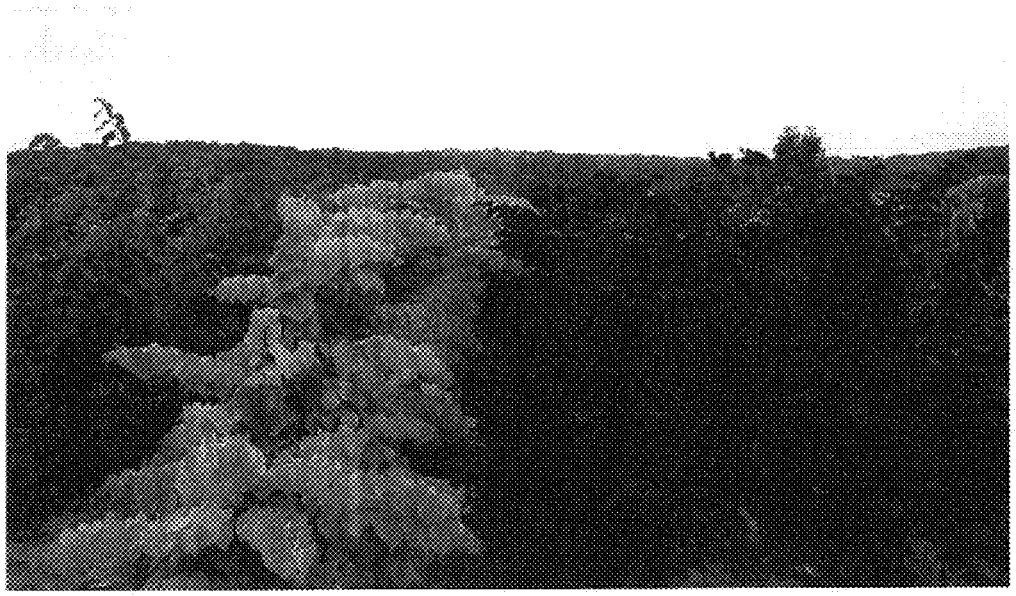
FIG. 5 shows an aerial view of the foliage color and form of 'Hearts of Gold' plants (center) compared to *Cercis canadensis* 'Forest Pansy' (purple foliage, right) and *Cercis canadensis* 'Appalachia Red' (green foliage, left).

The following is a detailed botanical description of the new and distinct variety of *Cercis canadensis* known as 'Hearts of Gold' based upon observation of the original four-year-old plant grown in Greensboro, N.C.

'Hearts of Gold' has not been observed under all possible environmental conditions. Where dimensions, sizes, colors and other characteristics are given, such characteristics are approximations or averages set forth as accurately as practicable. The phenotype of the variety may differ from the descriptions set forth herein with variations in environmental, climatic and cultural conditions.

'Hearts of Gold' is a small deciduous tree of *Cercis canadensis* useful for landscaping. 'Hearts of Gold' has distinct, bright golden foliage which is unusual for *Cercis canadensis* as these plants generally have medium-to-dark green leaves unless there is a nutrient deficiency. Unless otherwise indicated, 'Hearts of Gold' exhibits traits which are typical of other known cultivars of *Cercis canadensis*.

The color determinations have been made by reference to the 2001 edition of The Royal Horticultural Society Colour Chart except where general color terms of ordinary dictionary significance are used.

Family: Fabaceae.
Botanical classification:
- *Genus.*—*Cercis.*
- *Species.*—*canadensis.*

Variety denomination: 'Hearts of Gold'.
Common name: Eastern Redbud.
Use: Specimen tree.
Cultural requirements: Well-drained soils. Drought tolerant.
Light requirement: Full sun or partial shade.
Parentage. A chance seedling of *Cercis canadensis.*
Plant description:
- *Bloom period.*—March to April depending on location.
- *Plant habit.*—Small tree with upright stems and primary branches; smaller branches arch to produce a vase to rounded shaped canopy.
- *Vigor,*—Vigorous.
- *Dimensions at four years.*—Approximately 4 mm in height, 4 m to 4.5 m in width or spread.
- *Growth rate.*—Moderate to rapid when young. One-year-old budded plants produce approximately 1.8 m–2.1 m tall plants within one growing season. Older plants will grow at the rate of 0.8 m–0.6 m per year, and established specimens will grow at a further reduced rate.
- *Hardiness.*—USDA Zone 5.
- *Root system.*—Fibrous.
- *Propagation.*—Tissue culture or budding or grafting.
- *Disease and pest susceptibility.*—The species *Cercis canadensis* is native to the Southeastern U.S. and has relatively no disease or pest susceptibility. 'Hearts of Gold' is neither less nor more susceptible to pests or diseases than the species or in comparison to other cultivars of the species known to the inventor.

Trunk:
- *Dimensions.*—3.5 m in height, 9 cm in diameter at 1.5 m above ground.
- *Bark surface.*—Smooth.
- *Color.*—197B.
- *Lenticels.*—Numerous, tiny. Dimensions: 1 mm or less in diameter. Shape and aspect: Circular. Color: 152D.

Branches:
- *Color.*—197B.
- *Branch surface.*—Smooth.
- *Diameter* (*early season growth*).—2 cm to 4 cm.
- *Diameter* (*full season growth*).—3 cm to 6 cm.
- *Stem color* (*first season*).—146B.
- *Stem color* (*second season*).—199A to 200B or 200C.
- *Internode distance.*—Approximately 3 cm to 6 cm.
- *Lenticels.*—Numerous, tiny. Dimensions: 1 mm or less in diameter. Shape and aspect: Circular. Color: 152D.

Foliage:
- *Type.*—Deciduous.
- *Arrangement.*—Alternate.
- *Leaf.*—Shape: Broadly ovate. Margins: Entire. Apex: Acute. Base: Cordate. Surface texture (adaxial): Smooth and semi glossy. Surface texture (abaxial): Smooth. Dimensions (fully expanded leaves, 4 years old plant): 8 cm to 12 cm in length and 8 cm to 12 cm in width. Dimensions (fully expanded leaves, first and second year's young vigorous growth): 15 cm in length and 18 cm in width. Color (adaxial and abaxial surfaces): Emerging growth 31A, then varies with age of leaf from 151A, (youngest distal leaves) through 151B, 151C, and 151D (fully expanded proximal leaves) along the branch. Venation pattern: Reticulate.

*Petiole.*—Color: 178A. Surface: Smooth. Dimensions: 3 cm to 4 cm in diameter.

*Stipules.*—None.

*Fragrance.*—None observed.

*Fall leaf color.*—The following colors have all been observed: 13A, 14A, 14B, 15A, 15B, 16A.

*Causes for variations in color.*—Under conditions of bright sunlight, foliage retains bright golden color (151D) that grades to chartreuse-yellow (151A) over the course of the growing season. Under shaded growing conditions, including those imparted by the tree canopy, leaves will grade from bright golden to chartreuse-yellow to green (144A). However, even under these shaded conditions, plants retain the golden leaf color on the outermost leaves of the tree canopy. Golden foliage color is not affected by soil fertility or plant nutrient status. The unique color is not caused by lack of any known essential plant element, including iron, magnesium, or nitrogen.

Flowers:

*Blooming period.*—March to April, depending on location.

*Number of flowers per cluster.*—4 to 8.

*Type.*—Papillonaceous (pea-like).

*Arrangement.*—Sessile clusters.

*Location.*—Nodes of previous year's growth and along older trunks (cauliflory).

*Length of bloom.*—2–3 weeks.

*Fragrance.*—None.

*Flower dimensions.*—11 mm in length measured from keel to standard.

*Petals.*—Number: 5, lower 2 petals fused (collectively referred to as the keel). Standard or banner color: N78B. Keel petal color: N78B. Wing petal color: 77B. Calyx lobe color: N74C. Calyx base: fused. Calyx base color: 71A.

*Buds.*—Dimensions: 2 mm to 3 mm in length, and 1 mm to 1.4 mm in width. Shape: Broadly oval. Color: 61A. Number: Approximately 4 to 8 per cluster.

*Pedicel dimensions.*—1 cm in length and 2 mm to 3 mm in diameter.

*Pedicel color.*—N74C.

Reproductive organs:

*Stamen number.*—10.

*Stamen dimensions.*—Approximately 4 mm in length, less than 0.5 mm in diameter.

*Pistil number.*—1.

*Pistil dimensions.*—Approximately 5.3 mm to 5.5 mm in length, less than 1 mm in diameter.

Fruit:

*Shape.*—Leguminous.

*Color.*—200B to 200C becoming near black at maturity.

*Dimensions.*—5 cm to 10 cm in length and 10 mm to 13 mm in width.

*Arrangement.*—Borne along branches in a pendant manner.

*Lastingness.*—Though the winter months.

It is claimed:

1. A new and distinct variety of *Cercis canadensis* plant named 'Hearts of Gold', substantially as described and illustrated herein.

* * * * *